(12) United States Patent
Wieland et al.

(10) Patent No.: US 6,755,814 B2
(45) Date of Patent: Jun. 29, 2004

(54) IMPLANTABLE INFUSION PUMP WITH LEVEL MEASUREMENT

(75) Inventors: Manfred Wieland, Kiel (DE); Volker Zacharias, Kiel (DE); Jan Wierzoch, Mooregge (DE)

(73) Assignee: Codman Neuro Sciences Sarl, Le Locle (CH)

( * ) Notice: Subject to any disclaimer, the term of this patent is extended or adjusted under 35 U.S.C. 154(b) by 0 days.

(21) Appl. No.: 10/356,998

(22) Filed: Feb. 3, 2003

(65) Prior Publication Data

US 2003/0120262 A1 Jun. 26, 2003

Related U.S. Application Data

(63) Continuation-in-part of application No. 09/743,145, filed as application No. PCT/DE00/01631 on May 23, 2000, now abandoned.

(30) Foreign Application Priority Data

May 26, 1999 (DE) .......................................... 199 24 031

(51) Int. Cl.[7] .......................... A61K 9/22; A61M 37/00
(52) U.S. Cl. ..................................... 604/891.1; 604/132
(58) Field of Search ........................ 604/890.1, 891.1, 604/131, 132

(56) References Cited

U.S. PATENT DOCUMENTS

| 4,002,996 A | | 1/1977 | Klebanoff et al. |
| 4,354,506 A | | 10/1982 | Sakaguchi et al. |
| 4,360,019 A | * | 11/1982 | Portner et al. ............... 604/131 |
| 5,066,912 A | | 11/1991 | Kwiatkowski |

FOREIGN PATENT DOCUMENTS

| DE | 26 04 113 A1 | 2/1976 |
| DE | 35 20 782 A1 | 6/1985 |
| DE | 196 24 215 C1 | 6/1996 |

* cited by examiner

*Primary Examiner*—Michael J. Hayes
(74) *Attorney, Agent, or Firm*—Larson & Larson, PA; James E. Larson

(57) ABSTRACT

The invention relates to an implantable infusion pump comprising a housing, a base plate, a propellant chamber, a bellows having an internal volume for receiving a medicament to be administered to a patient, a constriction segment leading to a catheter placed in the body of the patient and communicating with the bellows internal volume, a resonant circuit formed by a coil, and a capacitor detecting the distance between a bottom surface of the bellows and the base plate. The coil is mounted on or in a bottom surface of the base plate and pointing towards the bellows bottom surface such that an inductance of the coil and a resonant frequency of the resonant circuit is a function of the distance between the bellows bottom surface the base plate.

19 Claims, 4 Drawing Sheets

IMPLANTABLE INFUSION PUMP WITH LEVEL MEASUREMENT

PRIOR APPLICATIONS

This application is a continuation-in-part of U.S. application Ser. No. 09/743,145, filed Jan. 5, 2001, now abandoned, which bases priority on International Application No. PCT/DE00/01631, filed May 23, 2000, which in turn bases priority on German Application No. DE 199 24 031.0, filed May 26, 1999.

BACKGROUND OF THE INVENTION

1. Field of Invention

This invention relates to an implantable infusion pump. More particularly, this invention relates to an improved implantable infusion pump having a casing, a base plate, a propellant chamber, a bellow mechanism and a constriction section, wherein the bellow mechanism includes a base member and an internal volume, the bellow mechanism internal volume receiving a medicant for delivery into a patient's body, and the constriction section communicating with the bellow mechanism internal volume and a catheter disposed within the patient's body.

2. Description of Prior Art

Infusion pumps are known in the prior art, such as those seen in German Patent Application D 226 04 113 C2, wherein the pump is implanted into a patient who is in need of a continuous supply of with medicament over a long period of time. An example of such a patient is one who is experiencing chronic pain or spastics.

It is known from DE 196 24 215 C1 to provide an infusion pump with an electromagnetic resonant circuit, wherein one element for level measurement is mechanically connected to the base of the bellows. However, the construction of this type of infusion pump is very complicated. Moreover, as the liquid level (medicament) decreases, the measurement accuracy of such liquid also decreases thereby not providing an accurate mechanism for monitoring the medicament level present within the pump.

SUMMARY OF THE INVENTION

The problem of the invention is to create an improved implantable infusion pump permitting for easier and more accurate level determination of the medicament within the pump.

The infusion pump according to the invention is advantageous in that the measurement accuracy increases as the liquid level decreases such that the accuracy is largest where it matters most, i.e., when the liquid is exhausted to very low levels. Moreover, the construction of the infusion pump is particularly easy and compact.

The problem underlying the invention is solved by an improved implantable infusion pump including a housing, a base plate, a propellant chamber, a bellow mechanism and a constriction section, the bellow mechanism having a base member and an internal volume, the bellow mechanism internal volume receiving a medicant for delivery into a patient's body, the constriction section communicating with the bellow mechanism internal volume and a catheter disposed within the patient's body. The improved pump of the present invention includes a resonant circuit having an inductance and a capacitance, the resonant circuit having a resonant frequency that is determined by a distance measured between the bellow mechanism base member and the pump base plate.

According to one embodiment of the invention, the inductance is provided by a resonant circuit coil, which is preferably constructed as a flat coil. The flatness of the flat coil allows for a compact design for the implantable infusion pump. The flat coil is disposed within a depression formed on a surface of the pump base plate directed towards the bellow mechanism base member. Thus, effects of coil stray fields are minimized. The pump base plate is electromagnetically shielded. Thus, the coil field is intensified in the direction of the base member of the bellow mechanism.

The capacitance for the resonant circuit is provided by a capacitor. Thus, the capacitance is easily adaptable to the circuit frequency needs. According to one embodiment of the present invention, the propellant chamber encloses the capacitor. This arrangement is particularly advantageous when the capacitor is located in a dead space of the propellant chamber such that the volume of the propellant chamber is more effectively used. However, the capacitor can be positioned on the side of the base plate which is opposite to the propellant chamber (i.e., the top surface). This position of the capacitor is particularly safe as the medicament in the bellow mechanism internal volume is separated from the capacitor by the strong barrier provided by the base plate. Advantageously, the capacitor is positioned adjacent to the base plate.

In another embodiment of the present invention, the capacitor is provided as a parallel plate capacitor having a first plate being provided by the base plate and a second plate being provided, in parallel, to the base plate. Thus, compactness of the pump is attained and is particularly large.

In yet another embodiment, the flat coil provides the capacitance for the resonant circuit. Thus, the need for a separate capacitor can be obviated with the result of the pump being particularly compact. The compactness can be optimized by providing a strong dielectric between the capacitor plates.

According to yet another embodiment, an electrically conductive coating is disposed along a bottom surface of the bellow mechanism base member. This enhances the accuracy of the liquid level measurement. Preferably, the conductive coating is constructed of copper. In an alternate embodiment however, the electrically conductive coating is chosen from other good conductors, such as gold.

DESCRIPTION OF THE DRAWINGS

The invention may be best understood by those having ordinary skill in the art by reference to the following detailed description when considered in conjunction with the accompanying drawings in which.

DETAILED DESCRIPTION OF THE PREFERRED EMBODIMENT

Figure 1:
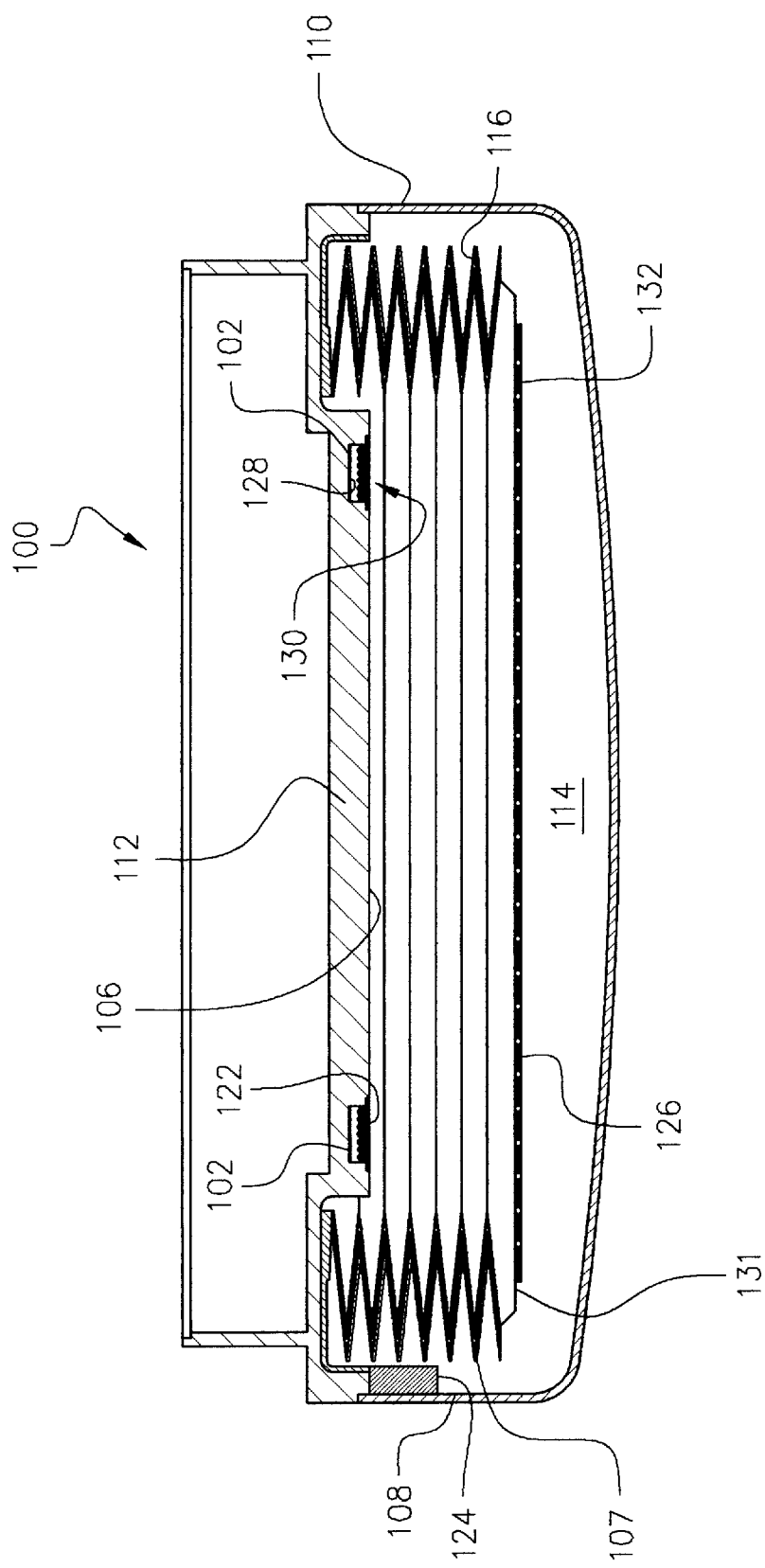
FIG. 1 is a cross-sectional view of an improved compact implantable infusion pump with level measurement of the present invention according to a preferred embodiment wherein a capacitor circuit element is employed.

An implantable infusion pump 100, a preferred embodiment, is shown in FIG. 1 having a casing 110, a base plate 112, a propellant chamber 114, a bellows 116 receiving a medicament to be delivered and a not shown constriction section leading to a catheter provided to be located in the body of a patient. The casing 110 is pressure proofed. A depression 102 is formed in a bottom surface 106 of the base plate 112 directed towards a base member 126 of the bellows 116 and receives a flat coil 122. A capacitor 124, located within the propellant chamber 114, is electrically coupled to the flat coil 122 thereby forming a resonant circuit. The capacitor 124 is advantageously placed between an outside diameter 107 of the bellows 116 and an inner side wall 108 of the casing 110. In this way, a small part of existing space for any pressurizing gas can be used to assemble the needed capacitor 124. The capacitor 124 is electrically connected to the flat coil 122 via isolated wires (not shown) outside of the propellant chamber 114. The flat coil 122 is electromagnetically shielded with respect to the base plate 112 by a $\mu$-metal element 128 that is essentially impermeable to magnetic fields. Moreover, relative to the propellant chamber 114 of the implantable infusion pump 100, and more particularly relative to the medicament chamber provided by the bellows 116 inside the propellant chamber 114, the flat coil 122 is enclosed within the depression 102 by a material cover 130 which is transparent to electromagnetic energy, such as, for example, a polymer film. On a bottom side 131 of the bellow base member 126, a thin coating of electrically conductive material 132 is employed in order to intensify the measuring effect. The electrically conductive material 132 could, for example, be made of copper or gold.

In an alternate embodiment of the preferred embodiment, of which is not shown in FIG. 1, a second capacitor is provided on a top surface of the base plate 112 (i.e., on the side which is opposite to the side facing bellows 116). The second capacitor is provided to facilitate tuning of the resonant circuit. The capacitance of the second capacitor can be relatively small.

Figure 2:
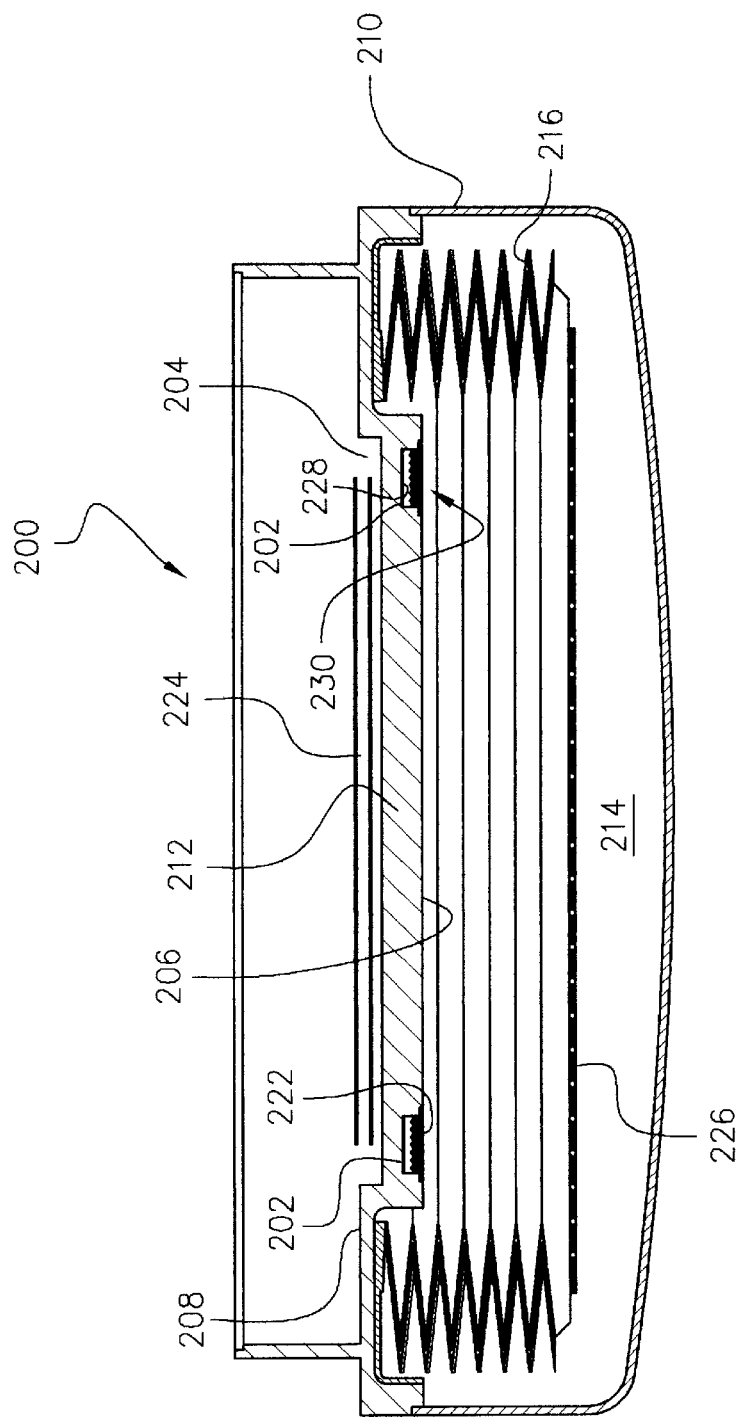
FIG. 2 is a cross-sectional view of an improved compact implantable infusion pump according to a second embodiment wherein a parallel plate capacitor is employed.

A second embodiment of an implantable infusion pump 200 of the present invention, which is shown in FIG. 2, includes a casing 210, a base plate 212, a propellant chamber 214, a bellows 216 for receiving a medicament to be delivered and a not shown constriction section leading to a catheter provided for location in the body of the patient. On a bottom surface 206 of the base plate 212, a first depression 202 is formed thereupon facing a base member 226 of the bellows 216 for receiving a flat coil 222. To reduce the required space, a disk-shaped parallel plate capacitor 224 lying flat on a top surface 208 of the base plate 212, opposed from the base plate bottom surface, is employed. A second depression 204 receiving the parallel plate capacitor 224 is formed in the top surface 208 of the base plate 212. The flat coil 222 is electromagnetically shielded with respect to the base plate 212 by a $\mu$-metal element 228 that is essentially impermeable to magnetic fields. Moreover, relative to the propellant chamber 214 of the implantable infusion pump 200, and more particularly relative to the medicament chamber provided by the bellows 216 inside the propellant chamber 214, the flat coil 222 is enclosed within the first depression 202 by a cover 230 made from a material which is transparent to electromagnetic energy.

Figure 3:
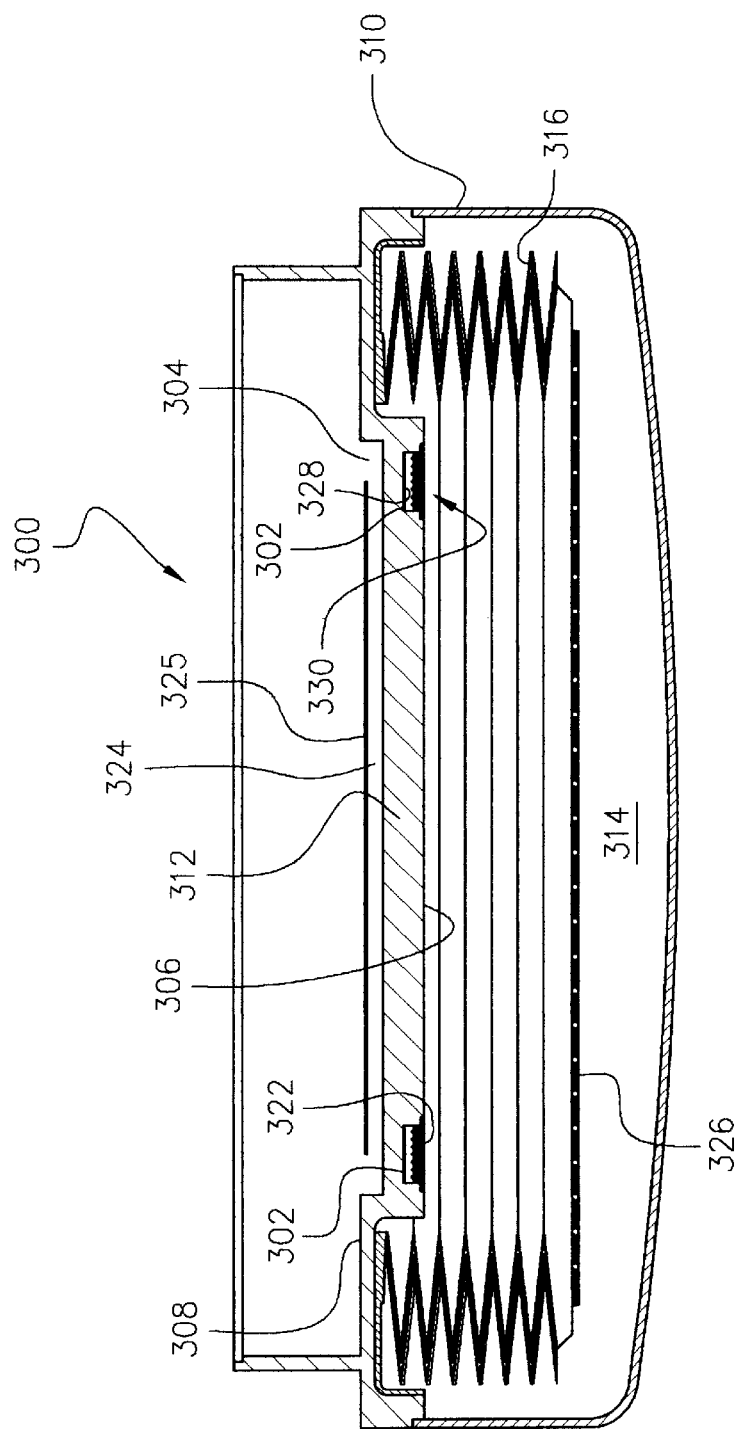
FIG. 3 is a cross-sectional view of an improved compact implantable infusion pump according to a third embodiment wherein an integrated parallel plate capacitor is employed.

A third embodiment of the implantable infusion pump 300 of the present invention is shown in FIG. 3, including a casing 310, a metal base plate 312, a propellant chamber 314, a bellows 316 for receiving a medicament to be delivered and a not shown constriction section leading to a catheter provided for location in the body of the patient. On a bottom surface 306 of the metal base plate 312, a first depression 302 is formed thereupon facing a base member 326 of the bellows 316 for receiving a flat coil 322. A flat disk 325 is placed on a conductive top surface 308 of the base plate 312 within a second depression 304 formed thereupon. The flat disk 325 is isolated against the conductive top surface 308 of the metal base plate 312. Accordingly, the flat disk 325 and the base plate top surface 308 form a capacitor 324. The flat coil 322 is electromagnetically shielded with respect to the base plate 312 by a $\mu$-metal element 328 that is essentially impermeable to magnetic fields. Moreover, relative to the propellant chamber 314 of the implantable infusion pump 300, and more particularly relative to the medicament chamber provided by the bellows 316 inside the propellant chamber 314, the flat coil 322 is enclosed within the first depression 302 by a cover 330 made from a material which is transparent to electromagnetic energy.

Regarding the above stated preferred, second and third embodiments, in the resonant circuit formed by the flat coil 122, 222, 322 and the capacitor 124, 224, 324, the flat coil 122, 222, 322 is the frequency-determining element since the inductance of the flat coil 122, 222, 322 effectively varies as the distance varies between the base member 126, 226, 326 and the base plate 116, 216, 316, while the capacitance of the capacitor 124, 224, 324 remains constant.

Figure 4:
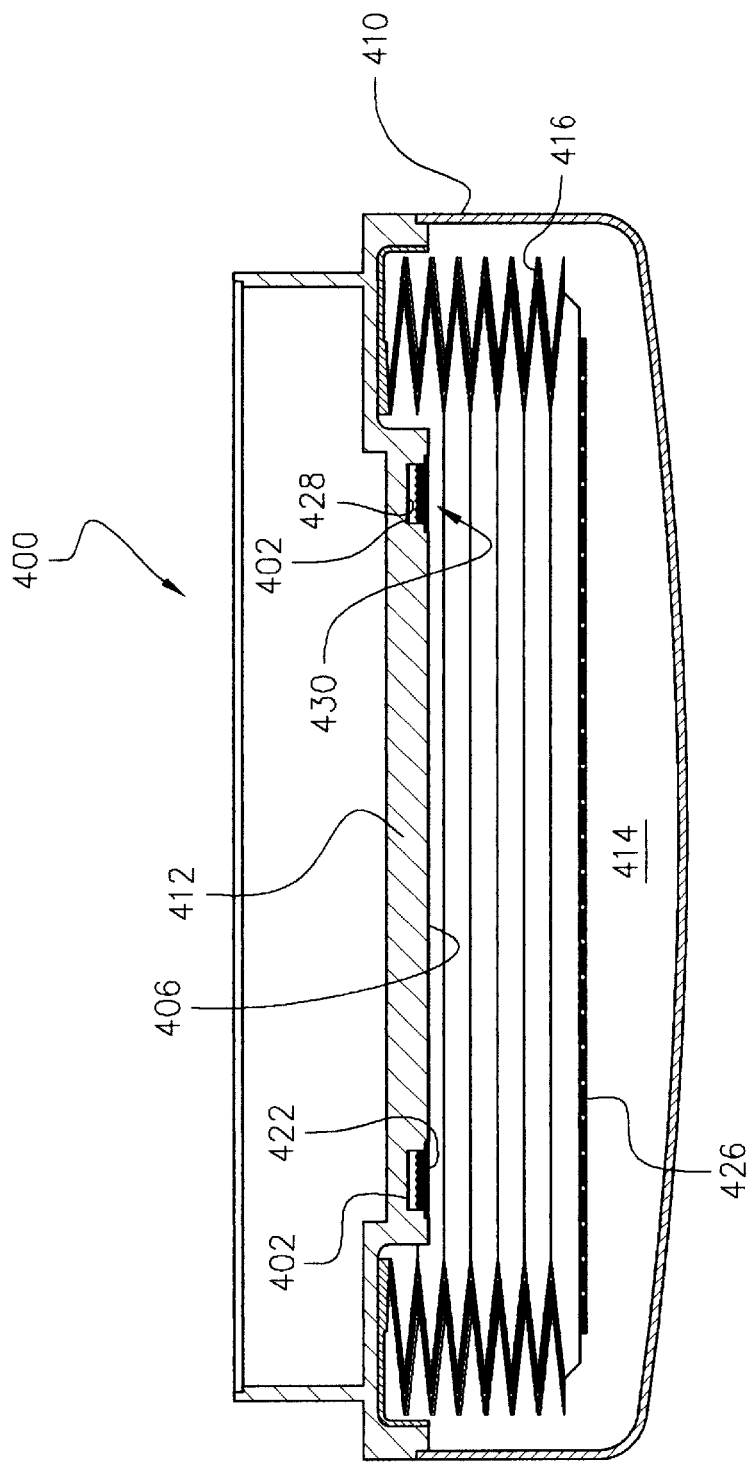
FIG. 4 is a cross-sectional view of an improved compact implantable infusion pump according to a fourth embodiment wherein a flat coil shaped in order to provide capacitance is employed.

A fourth embodiment of the implantable infusion pump 400 of the present invention, of which is shown in FIG. 4, includes a casing 410, a base plate 412, a propellant chamber 414, a bellows 416 for receiving a medicament to be delivered and a not shown constriction section leading to a catheter provided for location in the body of the patient. On a bottom surface 406 of the metal base plate 412, a depression 402 is formed thereupon facing a base member 426 of the bellows 416 for receiving a flat coil 422. The fourth embodiment differs from the preferred, second and third embodiments in that no separate capacitor is needed because the flat coil 422 serves as a capacitive element and the capacitance of the flat coil 422 in combination with the inductance of the flat coil 422 provides the resonant circuit. The flat coil 422 has a conductive part, and the isolated wires that form the coil have a distance between each winding because of isolation material of the wire and because of gaps caused by the round cross section of the wires and the filling factor. Advantageously, the flat coil 422 is shaped such that it is provided with a large surface that, in FIG. 4, is shown to face the ground of the depression 402 formed in the base plate bottom surface 406 that receives the flat coil 422. However, like in the cases of the preferred, second and third embodiments, the resonance frequency of the resonant circuit is essentially determined by the inductance of the flat coil 422 because this inductance effectively varies as the distance of the base member 426 to the base plate 412 varies, while the capacitance of the flat coil 422 remains essentially constant. The flat coil 422 is electromagnetically shielded with respect to the base plate 412 by a $\mu$-metal element 428 that is essentially impermeable to magnetic fields. Moreover, relative to the propellant chamber 414 of the implantable infusion pump 400, and more particularly relative to the medicament chamber provided by the bellows 416 inside the propellant chamber 414, the flat coil 422 is enclosed within the depression 402 by a cover 430 made from a material which is transparent to electromagnetic energy, such as, for example, polymeric film.

On energizing, the flat coil 122, 222, 322, 422 generates a primary electromagnetic field with a large aperture, which flows through the base 126, 226, 326, 426 of the bellows 116, 216, 316, 416 and induces eddy currents therein. In turn, these eddy currents generate a secondary magnetic field, which is coupled by means of the law of induction with the primary field. This coupling brings about change to the inductance of the flat coil 122, 222, 322, 422 and, thus, brings about a displacement, i.e., shift of the resonance frequency of the resonant circuit.

The rear shielding of the coil field by the μ-metal element 128, 228, 328, 428 firstly leads to a considerable reduction of the eddy currents in the base plate, 126, 226, 326, 426, i.e., the base member of the bellow mechanism. Secondly, there is an influencing of the phase of the upwardly directed field, i.e., away from the bellows 116, 216, 316, 416 so that there is an assisting action in the direction of the bellows 116, 216, 316, 416.

The inductance change does not take place through a change in the permeability, i.e., the magnetic conductivity of the coil environment, but instead by the coupling of the fields. Thus, the inductance is effectively varied.

The measuring effect is intensified by the application of a thin coating of a good electrical conductor (e.g., copper) on the under side of the bellows, in other words, on the bottom side of the bellows, such as in the case of the preferred embodiment shown in FIG. 1 where the base member 126 of the bellow mechanism 116 is coated with an electrically conductive layer of material 132, such as, for example, copper or gold.

A tilting of the base 126, 226, 326, 426 of the bellows relative to the base plate 112, 212, 312, 412 has no particular significance, because the differing spacings resulting from tilting largely compensate one another. The compensation is particularly good due to the large diameter of the flat coil 122, 222, 322, 422.

It is also advantageous that the accuracy of measurement increases with decreasing spacing between the base 126, 226, 326, 426 of the bellows 116, 216, 316, 416, i.e., as the volume of the bellows 116, 216, 316, 416 decreases.

All of the embodiments of the present invention effectively utilize the space provided within the housing thereby providing a much more compact design than those pumps shown in the prior art. Particularly, no additional space is needed to employ the capacitor within the housing. The compact configuration of the present invention is highly desirous since the pump must be implanted within the body of a patient. The more compact configuration of the novel pump provides less discomfort for the patient.

Equivalent elements can be substituted for the ones set forth above such that they perform the same function in the same way for achieving the same result.

Having thus described the invention, what is claimed and desired to be secured by Letters Patent is:

1. A compact implantable infusion pump comprising:
   a) a housing having a base plate and a propellant chamber disposed below the base plate, the base plate including a top and bottom surface and a depression formed in the base plate bottom surface,
   b) a bellow mechanism positioned within the housing propellant chamber underneath the housing base plate, the bellow mechanism having a base member and an internal volume, the bellow mechanism internal volume receiving a medicament for delivery into a patient's body,
   c) a constriction section communicating with the bellow mechanism internal volume and a catheter disposed within the patient's body for transferring the medicament into the patient's body from the bellow mechanism internal volume through the catheter and into the patient's body, and
   d) a resonant circuit including an inductance and a capacitance, the resonant circuit having a resonant frequency determined by a distance measured between the bellow mechanism base member and the housing base plate.

2. The compact implantable infusion pump according to claim 1, wherein the resonant circuit inductance is provided by a resonant circuit coil.

3. The compact implantable infusion pump according to claim 2, wherein the resonant circuit coil is constructed as a flat coil.

4. The compact implantable infusion pump according to claim 3, wherein the flat coil is disposed upon the housing base plate bottom surface and directed towards the bellow mechanism base member.

5. The compact implantable infusion pump according to claim 3, wherein the flat coil is disposed within the depression and directed towards the bellow mechanism base member.

6. The compact implantable infusion pump according to claim 1, wherein the housing base plate is electromagnetically shielded.

7. The compact implantable infusion pump according to claim 5, further comprising a material cover disposed upon the housing base plate bottom surface, the material cover transparent to electromagnetic energy, the flat coil enclosed within the depression by the material cover.

8. The compact implantable infusion pump according to claim 1, wherein the capacitance is provided by a capacitor.

9. The compact implantable infusion pump according to claim 8, wherein the capacitor is positioned within the propellant chamber.

10. The compact implantable infusion pump according to claim 8, wherein the capacitor is positioned on the housing base plate top surface.

11. The compact implantable infusion according to claim 10, wherein the capacitor comprises a pair of parallel plates such that a first plate is provided by the housing base plate top surface and a second plate is positioned in parallel to the housing base plate top surface directly thereabove.

12. The compact implantable infusion pump according to claim 8, wherein the capacitor is positioned directly above the base plate top surface.

13. The compact implantable infusion pump according to claim 3, wherein the flat coil is shaped as to provide the capacitance of the resonant circuit.

14. The compact implantable infusion pump according to claim 1, further comprising an electrical conductive coating disposed along a bottom surface of the bellow mechanism base member.

15. The compact implantable infusion pump according to claim 14, wherein the electrical conductive coating is chosen from the group consisting of gold and copper.

16. The compact implantable infusion pump according to claim 1, further comprising a variable tuning capacitor element for tuning the resonant circuit.

17. A compact implantable infusion pump comprising:
   a) a housing having a base plate and a propellant chamber disposed below the base plate, the base plate including a top and bottom surface and a depression formed in the base plate bottom surface,
   b) a bellow mechanism positioned within the housing propellant chamber underneath the housing base plate, the bellow mechanism having a base member and an internal volume, the base member having a bottom surface, the bellow mechanism internal volume receiving a medicament for delivery into a patient's body, c) a constriction section communicating with the bellow mechanism internal volume and a catheter disposed within the patient's body for transferring the medicament into the patient's body from the bellow mechanism internal volume through the catheter and into the patient's body, d) an electrical conductive coating disposed along the bellow mechanism base member bottom surface, e) a material cover disposed upon the housing base plate bottom surface, the material cover transparent to electromagnetic energy, and f) a resonant circuit including an inductance and a capacitance, a resonant frequency determined by a distance measured between the bellow mechanism base member and the housing base plate and a flat coil disposed within the depression.

18. The compact implantable infusion pump according to claim 17, further comprising a capacitor disposed within the housing, the capacitor providing the capacitance and the flat coil providing the inductance for the resonant circuit.

19. The compact implantable infusion pump according to claim 17, wherein the flat coil provides both the capacitance and the inductance for the resonant circuit.

* * * * *